United States Patent

Moeller et al.

[11] Patent Number: 5,981,819
[45] Date of Patent: Nov. 9, 1999

[54] PROCESS OF GENERATING $C_3$- AND $C_4$-OLEFINS FROM A FEED MIXTURE CONTAINING $C_4$ TO $C_7$ OLEFINS

[75] Inventors: Friedrich-Wilhelm Moeller, Friedrichsdorf; Peter Koenig, Frankfurt am Main; Christopher Higman, Schwalbach; Hans-Dieter Holtmann, Boenen, all of Germany

[73] Assignee: Metallgesellschaft Aktiengesellschaft, Frankfurt am Main, Germany

[21] Appl. No.: 08/970,931

[22] Filed: Nov. 14, 1997

[30] Foreign Application Priority Data

Nov. 26, 1996 [DE] Germany .............................. 19648795

[51] Int. Cl.[6] .............................. C07G 4/02; C10G 11/02; C10G 9/36
[52] U.S. Cl. ......................... 585/653; 585/648; 585/649; 208/120; 208/130
[58] Field of Search ..................................... 585/648, 653, 585/649; 208/120, 130

[56] References Cited

U.S. PATENT DOCUMENTS

| | | | |
|---|---|---|---|
| 4,980,053 | 12/1990 | Li et al. | 208/120 |
| 5,063,187 | 11/1991 | Burgfels et al. | 502/71 |

FOREIGN PATENT DOCUMENTS 0 369 364 B1   5/1990   European Pat. Off. .

*Primary Examiner*—Marian G. Knode
*Assistant Examiner*—In Suk Bullock
*Attorney, Agent, or Firm*—Herbert Dubno; Jonathan Myers

[57] ABSTRACT

A feed mixture containing $C_4$-olefins to $C_7$-olefins is evaporated and mixed with steam in a weight ratio of $H_2O$:hydrocarbons in the range from 0.5:1 to 3:1. The steam containing feed mixture with an inlet temperature in the range from 380° to 500° C. is introduced into a reactor, which contains a bed of granular, form-selective zeolite catalyst. The zeolite is of the pentasil type and has an atomic ratio of Si:Al of 10:1 to 200:1. From the bed a product mixture is withdrawn whose temperature is 20° to 80° lower than the inlet temperature, and whose total content of propylene and butene isomers is at least 60 wt-% of the olefinic constituents of the feed mixture.

3 Claims, 1 Drawing Sheet

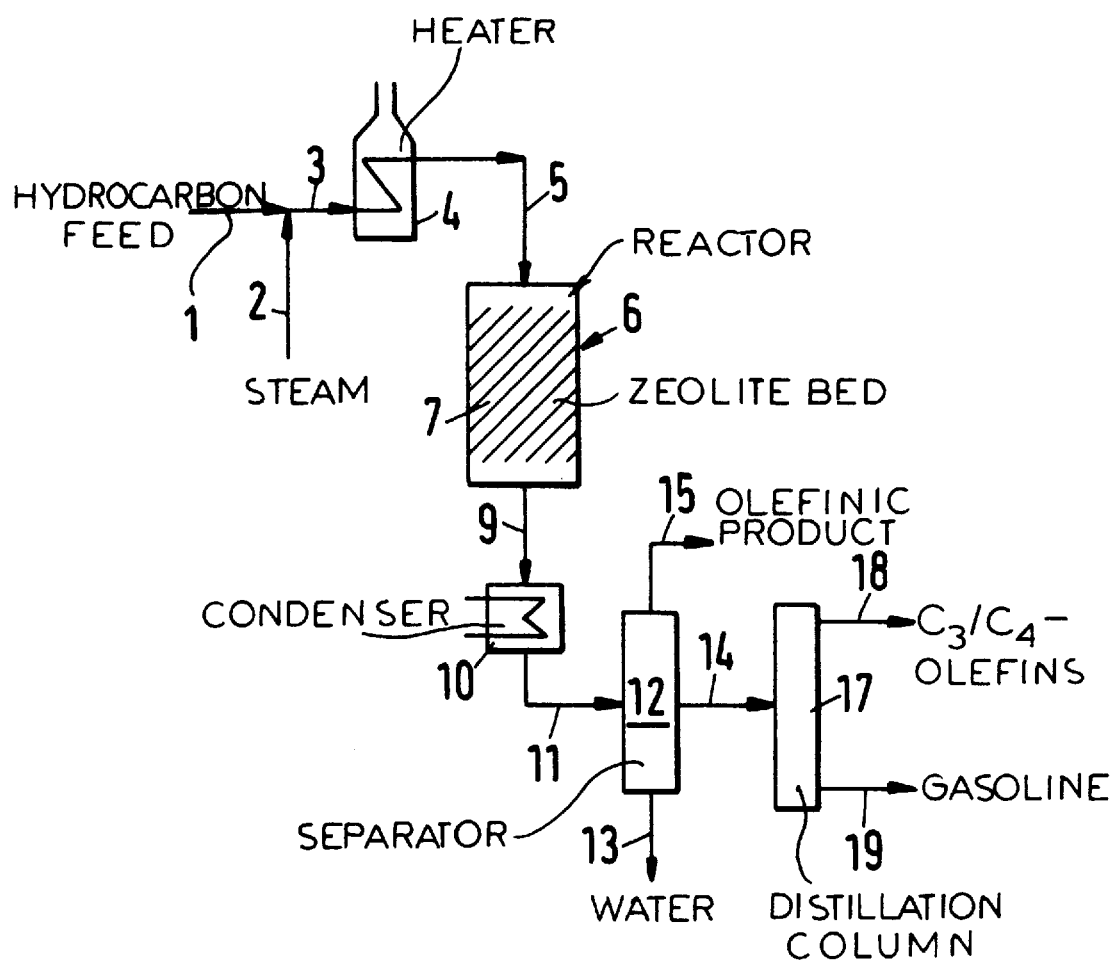

PROCESS OF GENERATING C$_3$- AND C$_4$-OLEFINS FROM A FEED MIXTURE CONTAINING C$_4$ TO C$_7$ OLEFINS

FIELD OF THE INVENTION

Our present invention relates to a process for producing C$_3$-olefins and C$_4$-olefins from a feed mixture containing C$_4$-olefins to C$_7$-olefins by conversion of the feed mixture on a granular zeolite catalyst at a temperature from 380° to 700° C.

BACKGROUND OF THE INVENTION

A process of this type is known from U.S. Pat. No. 5,059,735. In this process, a large amount of propane (a C$_3$-alkane) is added to the feed mixture containing C$_4$-olefins to C$_7$-olefins before it is passed over the catalyst, and in addition to C$_2$-olefins to C$_4$-olefins a considerable amount of C$_6$ and higher aromatics is generated.

OBJECTS OF THE INVENTION

The principal object of the present invention is to provide an improved process for converting C$_4$-olefins, C$_5$-olefins, C$_6$-olefins and C$_7$-olefins to C$_3$-olefins and C$_4$-olefins in an inexpensive manner and such that the product is rich in propylene.

Another object of the invention is to provide an improved process of the type described which overcomes drawbacks of the earlier system.

SUMMARY OF THE INVENTION

In accordance with the invention, this is accomplished in that the feed mixture is evaporated and mixed with steam. With a weight ratio of H$_2$O:hydrocarbons in the range from 0.5:1 to 3:1. The steam-containing feed mixture with an inlet temperature in the range from 380° to 700° C. is introduced into a reactor which contains a bed of granular, form-selective zeolite catalyst, where the zeolite is of the pentasil type and has an atomic ratio of Si:Al in the range from 10:1 to 200:1. From the bed and from the reactor a product mixture is withdrawn at a temperature of 20° to 80° C. lower than the inlet temperature, and whose total content of propylene and butene isomers is at least 60 wt-% and preferably at least 70 wt-% of the olefinic constituents of the feed mixture.

Usually, the product mixture also contains ethylene in an amount of 5 to 20 wt-%, based on the olefinic constituents in the carburizing or feed mixture.

Preferably, the temperature of the product mixture is lower by 30° to 50° C. than the inlet temperature.

The catalyst can be one which is known per se and described for instance in EP-B-0 369 364.

Advantageously, the reactor is operated at relatively low pressures in the range from 0.2 to 3 bar. Usually, the pressures in the reactor are in the range from 0.6 to 1.5 bar.

The composition of the carburization of feed mixture may vary within wide limits, and it is preferred to adjust the content of aromatics, calculated anhydrous, to not more than 5 wt-% and preferably not more than 2 wt-%. This is desirable because a higher content of aromatics leads to a premature degradation of the catalyst through carbon deposits. It is furthermore advantageous for the carburizing mixture to be free from components having carbon-carbon triple bonds or conjugated double bonds, as they likewise deactivate the catalyst. Suitable carburizing mixtures include, for instance, gas mixtures produced in a refinery, which may possibly be subjected to a hydrogenating pretreatment.

BRIEF DESCRIPTION OF THE DRAWING

The above and other objects, features, and advantages will become more readily apparent from the following description and examples provided in conjunction with the sole FIGURE of the accompanying drawing which is a flow diagram of the process of the invention.

SPECIFIC DESCRIPTION

Evaporated feed or carburizing mixture is supplied via line 1 and mixed with steam from line 2. Via line 3, the mixture is then passed through a heater 4, which is preferably designed as a fired heater. In line 5, the steam-containing carburizing mixture has a temperature in the range from 380° to 700° C., and preferably from 400° to 600° C. With this operating temperature it is introduced into the reactor 6. In the mixture in line 5, the weight ratio of H$_2$O:hydrocarbons is 0.5:1 to 3:1, preferably at least 1:1.

In the reactor 6, the granular zeolite catalyst is provided in the form of a bed 7. The grain sizes of the catalyst usually lie in the range from 1 to 8 mm. The zeolite is of the pentasil type, and it has form-selective properties. It is important for the zeolite catalyst that the primary crystallites of the alumosilicate have a narrow grain-size distribution with diameters in the range from 0.1 to 0.9 $\mu$m. The BET surface usually is 300 to 600 m$^2$/g, and the pore volume (according to mercury porosimetry) is about 0.3 to 0.8 cm$^3$/g. As a binder for holding the primary crystallites together, alumina hydrate is preferably used.

The conversion in the reactor 6 is preferably effected adiabatically, so that the temperature of the mixture to be converted decreases when the same flows through the bed 7. As a result, the product mixture withdrawn via line 9 has a temperature which is 20° to 80° C. and usually 30° to 50° C. lower than the inlet temperature in line 5. The main product of the product mixture in line 9 is propylene. 80 to 100 wt-% of the olefins in the carburizing mixture of line 5 are converted in the reactor 6.

In the cooler 10 the product mixture of line 9 is cooled to temperatures of about 30° to 60° C., so that water and gasoline will condense out. Via line 11, the condensate-containing mixture is supplied to a separator 12. From the separator 12 water is withdrawn via line 13, in line 14 an organic liquid phase is obtained, and via line 15 a product gas is withdrawn. The product gas contains C$_2$-olefins to C$_4$-olefins and in addition a small amount of paraffins. To separate the valuable substances, in particular ethylene and propylene, the gas of line 15 is supplied to a non represented separating means, which is known per se.

In the distillation column 17, the organic liquid phase of line 14 is separated into C$_3$-olefin and C$_4$-olefin fraction, withdrawn via line 18, and gasoline, withdrawn via line 19. The overhead product, which is withdrawn via line 18, usually still contains small amounts of saturated hydrocarbons. The gasoline in line 19 only contains small amounts (not more than 5 wt-%) of aromatics. The propylene-containing product of line 18 is usually likewise supplied to a separating means not represented here, so as to recover desired useful substances for instance through distillation or through adsorption. In addition to propylene, these useful substances include above all ethylene, n-butene-1 and isobutylene. n-butene-2 produced, for which there is no use, may be recirculated to the reactor 6.

EXAMPLES

In the laboratory, there is employed a plant corresponding to the drawing. The catalyst always is the same, and it is employed in the form of extrudates of the dimensions 1.5×3 mm. The catalyst has been described in detail in Examples 1 to 5 of the patent EP-B-0 369 364 (Suedchemie).

Example 1

The following carburizing mixture is prepared:

| | | |
|---|---|---|
| n-pentene-1 | ($C_5H_{10}$) | 40 wt % |
| n-hexene-1 | ($C_6H_{12}$) | 20 wt % |
| n-pentane | ($C_5H_{12}$) | 20 wt % |
| n-hexane | ($C_6H_{14}$) | 20 wt % |

For each kilogram of the olefins, 1.5 kg water is added to the carburizing mixture, the mixture is heated to 460° C., and at a pressure of 0.5 bar is passed through the reactor 6, which contains the catalyst bed 7. The loading per hour is 1 kg hydrocarbons per kg catalyst. The product mixture, which is withdrawn from the reactor at a temperature of 435° C., contains

| | | |
|---|---|---|
| | ethylene | 4.8 wt % |
| | propylene | 23.5 wt % |
| | isobutylene | 7.7 wt % |
| | n-butene-1 | 2.0 wt % |
| | c-butene-2 | 2.9 wt % |
| | t-butene-2 | 3.6 wt % |
| Total: | $C_2$–$C_4$-olefins | 44.5 wt % |

Example 2

The carburizing mixture of Example 1 together with 1.5 kg water per kg hydrocarbons is preheated to 500° C., and at a pressure of 2 bar and the loading of 3 kg/kg/h (calculated anhydrous) is passed through the catalyst bed. The product mixture in line 9 has been cooled to 470° C. and contains 41.6 wt-% olefins of the following composition:

| | |
|---|---|
| ethylene | 9.9 wt % |
| propylene | 48.6 wt % |
| butene | 41.5 wt % |

Example 3

Example 2 is modified such that there is now employed a pressure in the reactor 6 of 1.3 bar and a loading of the catalyst of 2 kg/kg/h (calculated anhydrous). The temperature in line 9 is 462° C., and behind the cooler 10, the temperature in line 11 has decreased to 35° C. After the separation of water, which contains a small amount of organic compounds, the following remains as liquid and gaseous product:

| | | Olefins | Paraffins | Naphthenes | Aromatics | Total |
|---|---|---|---|---|---|---|
| 1. C2–C4 Olefins: | | | | | | |
| C2 | (wt %) | 7.22 | | | | |
| C3 | (wt %) | 26.07 | | | | |
| C4 | (wt %) | 18.33 | | | | |
| Total | (wt %) | 51.62 | | | | 51.62 |
| 2. Combustion gas | | | | | | |
| C1 | (wt%) | | 0.13 | | | |
| C2 | (wt %) | | 0.31 | | | |
| C3 | (wt %) | | 2.1 | | | |
| C4 | (wt %) | | 2.05 | | | |
| Total | (wt %) | | 4.59 | | | 4.59 |
| 3. Gasoline | | | | | | |
| C5 | (wt %) | 5.17 | 16.19 | 0.51 | | |
| C6 | (wt %) | 1.13 | 15.94 | 0.8 | 0.4 | |
| C7+ | (wt %) | 0.62 | 0.85 | 0.45 | 1.73 | |
| Total | (wt %) | 6.92 | 32.98 | 1.76 | 2.13 | 43.79 |
| In all: | (wt %) | | | | | 100 |

Example 4

The following carburizing mixture is prepared, and the procedure is as described in Example 3:

| | |
|---|---|
| t-butene-2 | 9.2 wt % |
| n-pentene-1 | 35.9 wt % |
| n-hexene-1 | 18.3 wt % |
| n-pentene | 18.3 wt % |
| n-hexene | 18.3 wt % |

Upon removal of the water through line 13 a $C_2$- to $C_4$-olefin fraction of the following composition is obtained in combined lines 14 and 15:

| | |
|---|---|
| ethylene | 12.1 wt % |
| propylene | 49.7 wt % |
| isobutylene | 17.5 wt % |
| n-butene-1 | 5.3 wt % |
| c-butene-2 | 7.1 wt % |
| t-butene-2 | 8.3 wt % |

This olefin fraction constitutes 57.2 wt-% of the organic substances of the combined lines 14 and 15.

We claim:

1. A process for producing $C_3$-olefins and $C_4$-olefins from a feed mixture consisting essentially of $C_4$- to $C_7$-olefins, said feed mixture having a content of aromatics, calculated anhydrous, of up to 2 wt.-%, which comprises the steps of:

(a) evaporating said feed mixture and mixing said feed mixture with steam in a weight ratio of $H_2O$:hydrocarbons of 0.5:1 to 3:1 to form a steam-containing feed mixture;

(b) introducing said steam-containing feed mixture with an inlet temperature of 380° C. to 500° C. into a reactor containing a fixed bed of granular, form-selective zeolite catalyst where the zeolite is of the pentasil type with an atomic ratio of Si:Al of 10:1 to 200:1, said zeolite catalyst having a BET surface of 300 to 600 m²/g and the grain sizes of the primary crystallites of the aluminosilicate of the catalyst being in the range from 0.1 to 0.9 μm, adiabatically reacting the steam-containing feed mixture on said fixed bed at a temperature between 380° C. and 500°;

c) withdrawing from said reactor and from said bed a product mixture at a temperature of 20° to 80° C. lower than said inlet temperature and with a total content of propylene and butene isomers which is at least 60 weight % of olefinic constituents of the feed mixture;

(d) cooling said product mixture to a temperature of about 30° to 60° C. and condensing water out of said product mixture; and (e) separating condensed water from said product mixture and recovering a product gas consisting essentially of $C_2$ to $C_4$ olefins, and leaving an organic liquid phase.

2. The process defined in claim 1, further comprising the step of maintaining a pressure in said reactor during step (b) in a range of 0.2 to 3 bar.

3. The process defined in claim 1 wherein according to step (b) the catalyst has a pore volume of about 0.3 to 0.8 $cm^3/g$.

* * * * *